United States Patent
Ueno

(10) Patent No.: US 7,732,487 B2
(45) Date of Patent: Jun. 8, 2010

(54) METHOD FOR TREATING A DISEASE OR CONDITION RESPONSIVE TO OPENING OF C1C-2 CHANNEL

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 240 days.

(21) Appl. No.: 10/298,062

(22) Filed: Nov. 18, 2002

(65) Prior Publication Data

US 2003/0166632 A1 Sep. 4, 2003

Related U.S. Application Data

(60) Provisional application No. 60/331,542, filed on Nov. 19, 2001.

(51) Int. Cl.
*A61K 31/215* (2006.01)
*A61K 31/19* (2006.01)

(52) U.S. Cl. .................... 514/530; 514/573

(58) Field of Classification Search ............ 514/530, 514/573, 912
See application file for complete search history.

(56) References Cited

U.S. PATENT DOCUMENTS

| | | |
|---|---|---|
| 5,096,927 A | 3/1992 | Ueno et al. |
| 5,100,647 A | 3/1992 | Agus et al. |
| 5,164,415 A | 11/1992 | Ueno |
| 5,166,174 A | 11/1992 | Ueno et al. |
| 5,225,439 A | 7/1993 | Ueno et al. |
| 5,254,588 A | 10/1993 | Ueno et al. |
| 5,256,696 A | 10/1993 | Ueno et al. |
| 5,284,858 A | 2/1994 | Ueno et al. |
| 5,317,032 A | 5/1994 | Ueno et al. |
| 5,380,709 A | 1/1995 | Ueno et al. |
| 5,428,062 A | 6/1995 | Ueno et al. |
| 5,739,161 A | 4/1998 | Ueno |
| 5,886,034 A | 3/1999 | Ueno et al. |
| 6,015,828 A | 1/2000 | Cuppoletti |
| 6,265,440 B1 | 7/2001 | Ueno et al. |
| 6,414,016 B1 | 7/2002 | Ueno |
| 6,469,062 B2 | 10/2002 | Ueno et al. |
| 6,566,398 B1 | 5/2003 | Ueno |
| 2003/0130352 A1 | 7/2003 | Ueno et al. |

FOREIGN PATENT DOCUMENTS

| | | |
|---|---|---|
| CA | 2027814 C | 4/1991 |
| CA | 2030344 C | 5/1991 |
| CA | 2030345 C | 5/1991 |
| CA | 2030346 C | 5/1991 |
| CA | 2041417 C | 11/1991 |
| CA | 1312014 C | 12/1992 |
| CA | 1323364 C | 10/1993 |
| CA | 2150287 C | 12/1995 |
| CA | 2279267 A1 | 6/1999 |
| CA | 2377661 A1 | 1/2001 |
| CA | 2404767 A1 | 10/2001 |
| EP | 0 424 156 A2 | 4/1991 |
| EP | 0435443 A2 | 7/1991 |
| EP | 0978284 A1 | 2/2000 |
| JP | 2-32055 A | 2/1990 |
| WO | 01/76593 A2 | 10/2001 |
| WO | 02/20007 A1 | 3/2002 |
| WO | 02/089812 A1 | 11/2002 |

OTHER PUBLICATIONS

John Cuppoletti, Danuta H. Malinowska, Kirti P. Tewari. Qui-Ju Li, Ann M. Sherry, Myra L. Patchen, and Ryuji Ueno; SPI-0211 activates T84 cell chloride transport and recombinant human CIC-2 chloride currents; Am. J. Cell Physiol. 287: C1173-C1183, 2004.

Lubiprostone; Drugs of the Future 2004, 29(4): 336-341.

Lubiprostone RU 0211, SPI 0211; Drugs in R & D, Adis International, Auckland, NZ, vol. 6, No. 4, 2005, pp. 245-248.

John Cuppoletti, et al. "C1C-2 Cl Channels in human lung epithelia: activation by arachidonic acid, amidation, and acid-activated omeprazole" American Journal of Physiol Cell Physiol 281: C46-C54, 2001.

Akira Ikari, et al. "Prostaglandin $E_2$-Activated Housekeeping Cl-Channels in the Basolateral Membrane of Rat Gastric Parietal Cells" Japanese Journal of Physiology, 49, 365-372, 1999.

Teodor G. Paunescu, et al. "$PGE_3$ Activation of Apical Membrane Cl- Channels in A6 Epithelia: Impedance Analysis" Biophysical Journal vol. 81 Aug. 2001, 852-866.

*Primary Examiner*—Zohreh A Fay
(74) *Attorney, Agent, or Firm*—Sughrue Mion, PLLC

(57) ABSTRACT

Disclosed is a method for prophylactic or therapeutic treatment of a condition or disease responsive to opening of ClC-2 channel, which comprises the step of administrating an effective amount of a ClC-2 channel opener to a subject in need of said treatment. According to the invention, a tissue or organ to be transplanted can also be treated with the ClC-2 channel opener.

7 Claims, No Drawings

METHOD FOR TREATING A DISEASE OR CONDITION RESPONSIVE TO OPENING OF ClC-2 CHANNEL

This application claims benefit of Provisional Application No. 60/331,542 filed Nov. 19, 2001; the disclosure of which is incorporated herein by reference.

TECHNICAL FIELD

The present invention relates to a method for treating a disease or a condition responsive to opening of ClC-2 channel.

BACKGROUND ART

A chloride channel is an ion-transport membrane protein for transporting chloride ions ($Cl^-$). It has been reported that various kinds of chloride channels are present in the cell membrane of nerve, muscle and epithelium, and they are involved with various physiological functions and cytophylaxis mechanisms.

For example, a chloride channel cloned from crampfish's electric organ and named ClC-0 was later found to form a large family (ClC family). Examples of ClC family are: ClC-1 present in the skeletal muscle of mammals; ClC-2 present in the epithelium of various organs; ClC-3 and ClC-4 distributed in hippocampus, cerebellum, etc.; ClC-5 present in lung, kidney, etc.; ClC-6 and ClC-7 present in brain, testis, skeletal muscle, kidney, etc.; and ClCK-1 and ClCK-2 specifically shown only in kidney.

It is generally said that various channels are involved with a number of diseases. It is generally believed that the dysfunctioning of these channels or the existence of regulation defects in processes that activate such channels may play an important role in the pathogenesis of such diseases and illnesses. As a result, a compound, which opens various channels and assists regulation of electrophysiological function of cells, could have important therapeutic and prophylactic abilities for treatment and relief of such conditions.

It is inferred that a ClC-2 channel therapeutically plays an important role in cystic fibrosis, which is an autosomal recessive inherited disease best known in the Caucasian race (Cuppoletti et al., American Journal of Physiology. Cell Physiology, 281(1), C46-54, 2001; Joo et al., Biochemica et Biophysica Acta, 1446(3), 431-437, 1999 and Schwiebert et al., Proc. Natl. Acad. Sci. USA 97(7), 3879-3884, 1998). However, the details of other roles are not known very well.

SUMMARY OF THE INVENTION

The present inventor has conducted intensive studies using a compound has an ability to open ClC-2 channel and found that a ClC-2 channel opener is effective for treatment of various diseases.

Namely, the present invention relates to a method for prophylactic or therapeutic treatment of a condition or disease responsive to opening of ClC-2 channel, which comprises administrating an effective amount of a ClC-2 channel opener to a subject in need of said treatment, provided that the disease is not cystic fibrosis. The present invention further relates to a method for treatment of a tissue or organ to be transplanted in a transplantation process, comprising the step of contacting the tissue or organ with a pharmaceutical composition comprising a ClC-2 channel opener as an active ingredient.

Further, the present invention also relates to a pharmaceutical composition for prophylactic or therapeutic treatment of a condition or disease responsive to opening of ClC-2 channel, which comprises a ClC-2 channel opener as an active ingredient, provided that the disease or condition is not cystic fibrosis. The present invention also relates to a pharmaceutical composition for treating a tissue or organ to be transplanted in a transplantation procedure, which comprises a ClC-2 channel opener as an active ingredient.

Further more, the present invention relates to use of a ClC-2 channel opener for manufacturing a pharmaceutical composition for prophylactic or therapeutic treatment of a condition or disease responsive to opening of ClC-2 channel, provided that the disease is not cystic fibrosis. The present invention also relates to use of a ClC-2 channel opener for manufacturing a pharmaceutical composition for treatment of a tissue or organ to be transplanted in a transplantation procedure.

The ClC-2 channel opener used in the present invention is not particularly limited and may be any compound as far as it has a ClC-2 channel opening activity. The ClC-2 channel opening activity may be confirmed by measuring the increase of chloride-ion flows through a ClC-2 channel in a cell membrane from inside to outside of the cell or in the opposite direction. For instance, it is possible to carry out a screening for a compound having ClC-2 channel opening activity by using a known assay strategy such as patch clamp method.

Examples of compounds having ClC-2 channel opening activity include cyclooxygenase inhibitor or nonsteroidal anti-inflammatory agent such as ibuprofen and ebselen, protein kinase A, oleic acid, elaidic acid, arachidonic acid, cell growth factor, such as $TGF_\alpha$, (transforming growth factor-α) and KGF (keratinocyte growth factor)), prostaglandin compound and benzimidazole derivative.

In the present invention, "a disease or a condition responsive to opening of ClC-2 channel" includes a condition, morbidity, disease and disorder prophylactically or therapeutically responsive or sensitive to activation or opening of ClC-2 channel in the cell of target tissues; and a condition, morbidity, disease and disorder prophylactically or therapeutically relate to ClC-2 channel behavior. As far as they are diseases or conditions responsive to ClC-2 channel opening, other than cystic fibrosis, there is no limitation. Examples of said diseases or conditions include hepatic disease such as hepatitis and cirrhosis, pancreatic disease such as pancreatitis, constipation, exocrine disorder such as dry eye and dry mouth, cerebral function disorder, cardiovascular system disorder, respiratory system disorder and digestive system disorder.

Accordingly, "subject in need of said treatment" may be a subject who is suffering from above-discussed condition or disease, or a subject who is susceptible to suffering from such condition or disease. The subject may be any mammalian subject including human beings.

According to the invention, a pharmaceutical composition comprising a compound having ClC-2 channel opening activity is administrated to a patient in need of such treatment. The pharmaceutical composition may be in a form suitable for systemic or topical application, which is to be administrated by oral, intravenous (including drip infusion), subcutaneous, intrarectal, intravaginal, percutaneous or ocular administration. Examples of dosage forms used in the instant invention comprise, but not limited to, internal preparation, injection, drips, external preparation, eye drops, suppository and pessary.

The dose of the active ingredient may vary according to the type of the subject such as animals or human, age, weight, symptom to be treated, desirable therapeutic effect, administration route and period for treatment, and a suitable dose may be chosen according to the compound to be used.

The pharmaceutical composition of the invention may further comprise physiologically acceptable, suitable additives in addition to the active ingredient. The term "additives" used herein is the generic name for the following: excipient, diluent, filler, resolvent, lubricant, adjuvant, binder, disintegrator, coating agent, encapsulating agent, ointment base, suppository base, aerosol, emulsifier, dispersant, suspension, thickener, isotonizing agent, buffer, soothing agent, preservative, antioxidant, corrigent, flavor, colorant and functional material such as cyclodextrin and biodegrading polymer. These additives are well known to the art and may be selected as desired based on descriptions in general books on pharmaceutics.

The term "treatment" used herein includes any means of control such as prevention, care, relief of the condition, attenuation of the condition and arrest of progression.

According to the present invention, the pharmaceutical composition comprising a ClC-2 channel opener as an active ingredient is effective for treatment of a disease or a condition responsive to opening of ClC-2 channel. Examples of the disease or condition may include hepatic disease, pancreatic disease, constipation, exocrine disorder, cerebral function disorder, cardiovascular system disorder, respiratory system disorder and digestive system disorder. Especially, the composition has an ability to promote secretion of chloride ion in organs that control fluid secretion. Said promotion of chloride ion secretion results in, for example, acceleration of bile secretion in liver, acceleration of intestinal fluid secretion in bowel, and acceleration of lacrimation and salivary secretions in exocrine system such as the lacrimal and salivary glands. Accordingly, the pharmaceutical composition of the invention is effective for treatment of hepatic disease, exocrine disorder such as dry eye and dry mouth and constipation.

The composition or method of the present invention is also effective for treatment of a tissue or organ to be transplanted in a transplantation procedure. By treating the tissue or organ with the composition of the invention, organ hypoactivity as well as concomitant disease, which may occur during or after the transplantation operation, are effectively prevented.

In the transplantation procedure, it is necessary not only to maintain the function of the tissue or the organ for a certain period until they are grafted to the recipient but also to ensure the tissue is well taken by the recipient after the surgery. The composition of the present invention may be used for treatment of a tissue or organ upon removal of the tissue or organ from the donor, for preservation and maintenance of the removed tissue or organ, for treatment of the tissue or organ as well as the recipient upon grafting surgery, and for post-operational treatment.

During the transplantation process, the pharmaceutical composition of the present invention may be administered in vivo to the donor or applied directly to the removed tissues or organs. For example, the composition may be used as a perfusate for in vivo perfusion of the donor at the removal operation, as a perfusate for ex vivo perfusion of the removed organ, as a preservative solution for the removed organ and as a rinse solution before blood reperfusion at grafting the organ to the recipient. The composition of the invention may be employed as either one of perfusate, preservative solution and rinse solution, or two or all of these solutions.

According to the present invention, the composition may contain a single active ingredient or a combination of two or more active ingredients. In a combination of plural active ingredients, their respective dose may be suitably increased or decreased in consideration of their therapeutic effects and safety.

Further, the composition of the present invention may contain other pharmaceutically active ingredients, as far as they are not contrary to the objects of the present invention.

The present invention will be described in more detail with reference to the following examples, which is not intended to limit the present invention.

EXAMPLE 1

(Method)

Test substance 1: 13,14-dihydro-15-keto-16,16-difluoro-prostaglandin $E_1$, which is a ClC-2 channel opener was used. The test substance 1 of 10 or 100 µg/kg in 5 mL/kg of the vehicle was orally administered to male Wistar rats (six weeks old, weight: 180-210 g) that had been fasted for at least 16 hours. The control group received the same volume of the vehicle (0.5% ethanol and 0.01% polysorbate 80 in distilled water). Thirty minutes after the administration, the animals underwent laparotomy under ether anesthesia. The first portion of the duodenum and end portion of the ileum were ligated respectively and the bowel was removed. The intestinal fluid of each animal was collected from the removed bowel and the amount was determined. After the intestinal fluid was centrifuged by 10,000×g for 5 minutes, its supernatant was collected. The chloride ion concentration in the supernatant was measured with a chloride counter (CL-7, Hiranuma Sangyo Co., Ltd.). Dunnett's test was used in comparing the control group and the test groups receiving test substance 1 in each dose. P values less than 0.05 were considered to be statistically significant.

(Result)

Table 1 shows the amount of the intestinal fluid and concentration of chloride ion in the intestinal fluid in each group.

TABLE 1

Effect of Test Substance 1 on the Amount of Intestinal Fluid and Concentration of Chloride Ion in Intestinal Fluid in Rat

| Group | Dose | n | Amount of Intestinal Fluid mL | Chloride Ion Concentration in Intestinal Fluid Mean ± S.E., mEq/L |
|---|---|---|---|---|
| Control | — | 7 | 0.9 ± 0.1 | 41.8 ± 3.9 |
| Test Sub. 1 | 10 µg/kg | 7 | 3.3 ± 0.3** | 110.1 ± 5.6** |
| Test Sub. 1 | 100 µg/kg | 7 | 5.3 ± 0.2** | 126.6 ± 2.4** |

Dunnett's Test: Compared with the Control Group, **$P < 0.01$

Administration of test substance 1 of 10 and 100 µg/kg increased the amount of intestinal fluid and chloride ion concentration in the intestinal fluid in a dose-dependant manner. Additionally, compared with the control group, there was a significant increase in the amount of intestinal fluid and the concentration of chloride ion in intestinal fluid in each of the groups receiving test substance 1.

The above result suggests that a ClC-2 channel opener positively accelerates the secretion of chloride ion in the bowel to increase the amount of intestinal fluid, and it is effective for treatment of constipation.

EXAMPLE 2

(Method)

An eye drop composition comprising 0.001% of the test substance 1 was instilled to male white rabbit in the amount of 30 μL/eye. The control group received the same amount of eye drop vehicle. Two hours after the instillation, without anesthesia, one third of palpebra inferior (on the ear side) was covered with the Schirmer's Paper (Showa Yakuhin Kako K. K., Japan, Lot No. 9011N) by binding its tip inside the conjunctival sac for 1 minute. Then the amount of lacrimal fluid was measured from the length of wetting area on the paper filter with the scale on it. Lacrimal fluid 5 μL was collected from the conjunctival sac of palpebra inferior with a capillary pipet. The collected lacrimal fluid was diluted five fold with distilled water and chloride ion concentration in the lacrimal fluid was measured with a chloride counter (CL-7, Hiranuma Sangyo Co. Ltd., Japan). Student's t-test and Wilcoxon's test were used in comparing the control group and the group receiving test substance 1. P values less than 0.05 were considered to be statistically significant.

(Result)

Table 2 shows the amount of lacrimal fluid and the chloride ion concentration in lacrimal fluid of each group.

TABLE 2

Effect of Test Substance 1 on the Amount of Lacrimal Fluid and the Chloride Ion Concentration in Lacrimal Fluid in Rabbit

| Group | Dose | n | Amount of Lacrimal Fluid mL | Chloride Ion Concentration in Lacrimal Fluid Mean ± S.E., mEq/L |
|---|---|---|---|---|
| Control | — | 8 | 6.8 ± 0.5 | 116.9 ± 1.3 |
| Test Sub. 1 | 0.001% | 8 | 11.5 ± 0.7## | 152.9 ± 7.7(##) |

Student's t-test: Compared with the Control Group, ##P < 0.01
Wilcoxon's test: Compared with the Control Group, (##)P < 0.01

Compared with the control group, there was a significant increase in the amount of lacrimal fluid and chloride ion concentration in lacrimal fluid in the group receiving test substance 1.

The above result suggests that a ClC-2 channel opener positively accelerates the secretion of chloride ion in the eye to increase the amount of lacrimal fluid, and it is effective for treatment of dry eye.

EXAMPLE 3

(Method)

Test substance 2: 13,14-dihydro-15-keto-16,16-difluoro-18(S)-methyl-prostaglandin $E_1$, which is a ClC-2 channel opener was used. Test substance 2 of 100 μg/kg was orally administered to male Wistar rats (six weeks old, weight: 180-210 g) three times a day for seven days. The control group received the same amount of the vehicle (0.01% polysorbate 80 and 0.5% ethanol in distilled water). In the following morning of the final administration day (about 17 hours after the final administration), a polyethylene catheter (PE10, Becton Dickinson and Company) was inserted into the rats' common bile duct under ether anesthesia. The rats were placed in a Borrmann's cage and were left for 1 hour to awake from anesthesia. Bile discharged during one hour from one to two hours after the insertion of the catheter was collected to measure the amount of bile. Chloride ion concentration was measured with a chloride counter (CL-7, Hiranuma Sangyo Co., Ltd.). Student's t-test was used in comparing the control group and the group receiving test substance 2. P values less than 0.05 were considered to be statistically significant.

(Result)

Table 3 shows the amount of bile and chloride ion concentration in bile in each group.

TABLE 3

Effect of Test Substance 2 on the Amount of Bile and chloride ion concentration in Bile in Rats

| Group | Dose | n | Amount of Bile mL | Chloride Ion Concentration in Bile Mean ± S.E., mEq/L |
|---|---|---|---|---|
| Control | — | 7 | 364.4 ± 26.1 | 91.1 ± 2.7 |
| Test Sub. 2 | 100 μg/kg | 8 | 491.9 ± 36.7* | 98.4 ± 1.8** |

Student's t-test: Compared with the Control Group, *P < 0.05

Compared with the control group, there was a significant increase in the amount of bile and chloride ion concentration in bile in the group receiving test substance 2.

The above result suggests that a ClC-2 channel opener positively accelerates the secretion of chloride ion in the liver to increase the amount of bile, and it is effective for treatment of hepatic disease as well as hepatic transplantation.

EXAMPLE 4

(Method)

Male Wistar rats were used. The common bile duct of both the test and the control groups were catheterized to collect bile under pentobarbital sodium anesthesia. After the catheter was inserted and fixed in the portal vein, Krebs-Ringer solution (pH 7.4, 37° C.) comprising sodium taurocolate (30 μmol/l) saturated with 95% $O_2$ and 5% $CO_2$ was infused at a constant flow rate of 4.0 mL/min/g liver weight by means of peristaltic pump. The liver was removed under perfusion. For the test group, test substance 2 was added to the Krebs-Ringer solution. Thirty minutes after the perfusion, the amount of bile of both the test group and the control group was measured. Chloride ion concentration in the bile was also measured. The amount of bile at 30 minutes after the administration of test substance 2 or vehicle was shown as relative value (%) to the amount immediately before the administration.

(Result)

Table 4 shows the amount of bile and chloride ion concentration in bile in each group.

TABLE 4

Effect of Test Substance 2 on the Amount of Bile
and chloride ion concentration in Bile in Rats

| Group | Concentration (µM) | n | Relative Amount of Bile (%) (Mean ± S.E.) | Chloride Ion Concentration in Bile µM/min/g liver (Mean ± S.E.) |
|---|---|---|---|---|
| Control | — | 5 | 92.4 ± 2.7 | 0.268 ± 0.007 |
| Test Sub. 2 | 10 | 5 | 126.2 ± 9.0** | 0.353 ± 0.009** |

Compared with the Control Group, **$P < 0.01$ (one-way ANOVA with Fisher's multiple comparison test)

Compared with the control group, there was a significant increase in the amount of bile and chloride ion concentration in bile in the group receiving test substance 2.

The above result suggests that a ClC-2 channel opener positively accelerates the secretion of chloride ion in the removed liver to increase the amount of bile. This result suggests that ClC-2 channel opener is effective for treatment in organ transplantation procedure including hepatic transplantation.

EXAMPLE 5

(Method)

Male Wistar rats (weight: about 280 g) were anesthetized with intraperitoneal injection of pentobarbital sodium (50 mg/kg) and hepatic-portal region was exposed by abdominal midline incision. The common bile duct was cannulated and the portal stem was inserted with a 19 gauge Surflo® needle equipped with a three way stopcock. Simultaneously, the liver was perfused with oxidized Krebs-Ringer Buffer at a rate of 4.0 mL/min/g liver and was bled by dissecting the inferior vena cava. The liver was cut off from the tissues around it, removed outside the body and subjected to extracorporeal perfusion. The liver was subjected to a 15-minute pre-perfusion until its oxygen consumption achieved to a constant state. Then the perfusate was replaced with an organ preservative solution (University of Wisconsin solution; (U-W solution) at 4° C. Immediately after the replacement was completed, the liver connected with the three-way stopcock was removed from the perfusion cycle and the inlet was clamped. Then the liver was put in the preservative solution (U-W solution) at the same temperature and stored for 16 hours. After the 16-hour storage, the liver was reperfused with Krebs-Ringer Buffer. Thirty minutes after the reperfusion, the amount of bile flow was measured.

(1) Effect of substance 2 added to the organ preservative solution (U-W solution)

In the above perfusion protocol, test substance 2 at the concentration of 10 µM was added to the preservative solution (U-W solution).

(2) Effect of substance 2 added to the perfusate during reperfusion

In the above perfusion protocol, test substance 2 was not added to the preservative solution, but added to the perfusate (Krebs-Ringer Buffer) for reperfusion at the concentration of 10 µM.

(Result)

Tables 5 and 6 respectively show the amount of bile flow at 30 minutes after the reperfusion under the (1) and (2) conditions.

TABLE 5

Organ Preservative Effect of Test Substance 2
Added to the Preservative Solution

| Group | Concentration (µM) | n | Amount of Bile Flow, µL/min/g liver (Mean ± S.D.) |
|---|---|---|---|
| Control | — | 5 | 2.11 ± 0.18 |
| Test Sub. 2 | 10 | 5 | 2.43 ± 0.10* |

Compared with the Control Group, *$P < 0.05$

TABLE 6

Effect of Substance 2 Added to the Perfusate
during Reperfusion

| Group | Concentration (µM) | n | Amount of Bile Flow, µL/min/g liver (Mean ± S.D.) |
|---|---|---|---|
| Control | — | 5 | 2.11 ± 0.18 |
| Test Sub. 2 | 10 | 5 | 2.67 ± 0.31* |

Compared with the Control Group, *$P < 0.05$

Compared with the control group, there was a significant increase in the amount of bile flow in the group receiving substance 2, which was added to the preservative solution and the perfusate during the reperfusion.

The above result suggests that a ClC-2 channel opener is effective for improving preservation of organs, inhibiting disorders during reperfusion and improving taking rate after transplantation, and therefore, it is effective for treatment in organ transplantation procedure including hepatic transplantation.

EXAMPLE 6

(Method)

Test substance 1 of 0.3 mg/kg in 10 mL/kg of vehicle was subcutaneously administered to ddY male mice (5 weeks old, weight: 27-30 g). The control group received the vehicle. Thirty minutes after the administration, the mice were beheaded with guillotine. Duration of gasping shown after beheading was measured.

(Result)

Table 7 shows the antianoxia effect in each group.

TABLE 7

| | Antianoxia Effect | | |
|---|---|---|---|
| Group | Dose (mg/kg) | n | Duration of Gasping (Mean ± S.D.) |
| Control | — | 10 | 20.3 ± 1.9 |
| Test Sub. 1 | 0.3 | 10 | 24.1 ± 1.9** | t-test: **$p < 0.01$

Compared to the control group, there was a significant increase in the duration of gasping in the group receiving test substance 1.

The above result suggests that a ClC-2 channel opener is effective for treatment of atmospheric hypoxia, hypoxia or anoxia in the brain.

EXAMPLE 7

(Method)

Test substance 1 of 0.1 or 0.01 mg/kg in 5 mL/kg of vehicle was subcutaneously administered to male Wistar rats (7 weeks old, weight: 200-250 g). The control group received the same amount of the vehicle (physiological Saline). Thirty minutes after the administration, ammonium sulfate 600 mg/mL was administered to the abdominal cavity of the rats. The survival rate at 30 minutes after the administration of ammonium sulfate was calculated. Animals that had survived until 30 minutes after the administration of ammonium sulfate were killed under chloroform, and their lungs were removed to measure the weights. Regarding animals that had been dead by 30 minutes after the administration of ammonium sulfate, their lungs were removed immediately after their death to measure the weights. The lung-weight of the respective groups was compared to the lung-weight of the normal group, which received no ammonium sulfate. Based on the lung-weight measurements, the inhibitory rate of lung-weight increase of the group receiving test substance 1 as compared to that of the control group was calculated.

(Result)

Table 8 shows the surviving rate and Table 9 shows the inhibitory rate of lung-weight increase.

TABLE 8

Antipneumonedema Effect (Surviving Rate)

| Group | Dose (mg/kg) | n | Surviving Rate (%) |
|---|---|---|---|
| Control | — | 10 | 30 |
| Test Sub. 1 | 0.1 | 10 | 60 |

TABLE 9

Antipneumonedema Effect (Inhibitory Rate of Lung-weight Increase)

| Group | Dose (mg/kg) | n | Inhibitory Rate of Lung-weight Increase (%) |
|---|---|---|---|
| Test Sub. 1 | 0.01 | 10 | 47 |

The above result suggests that a ClC-2 channel opener is effective for treatment of lung disorder.

EXAMPLE 8

(Method)

Effects on acute ulcer was determined by means of water-immersion restraint stress induced ulcer model and indomethacin induced ulcer model.

Test substance 1 was orally administered to male Wistar rats (weight: 180-210 g) that had been fasted for 24 hours. In the water-immersion restraint stress induced ulcer model, 10 minutes after the oral administration of test substance 1, the rats were bound in a stress cage and immersed in water at 23° C. up to the level of their chest xiphisternums. Six hours after the immersion, the animals were killed by cervical dislocation. In the indomethacin induced ulcer model, immediately after the oral administration of test substance 1 or 2, indomethacin 10 mg/kg was orally administered. Five hours after the administration, the animals were killed by cervical dislocation. The stomachs removed from the animals were fixed with 1% formalin and then dissected along the greater curvatures. The major axis (mm) of each ulcer formed in the stomach was measured. The major axes of the ulcers in each animal were totaled, which were expressed as ulcer coefficients. Based on the ulcer coefficients of the control group and those of the groups receiving test substances, the ulcer inhibitory rates were calculated.

(Result)

Table 10 shows the anti-water restrictive stress ulcer effect and Table 11 shows the anti-indomethacin ulcer effect.

TABLE 10

Anti-water Restrictive Stress Ulcer Effect

| Group | Dose (µg/kg) | n | Ulcer Coefficient (Mean ± S.E.) | Ulcer Inhibitory Rate (%) |
|---|---|---|---|---|
| Control | — | 10 | 29.3 ± 3.0 | — |
| Test Sub. 1 | 30 | 10 | 13.4 ± 2.0** | 54.3 |
| Test Sub. 1 | 100 | 10 | 4.3 ± 1.9** | 85.3 |

Compared with the Control Group, **$P < 0.01$ (Dunnett's test)

TABLE 11

Anti-indomethacin Ulcer Effect

| Group | Dose (µg/kg) | n | Ulcer Coefficient (Mean ± S.E.) | Ulcer Inhibitory Rate (%) |
|---|---|---|---|---|
| Control | — | 10 | 49.6 ± 7.6 | — |
| Test Sub. 1 | 2 | 10 | 27.9 ± 5.1 | 44 |
| Control | — | 10 | 86.4 ± 9.6 | — |
| Test Sub. 2 | 1 | 10 | 35.7 ± 8.3** | 58.7 |
| Test Sub. 2 | 3 | 10 | 30.0 ± 4.6** | 65.3 |
| Test Sub. 2 | 10 | 10 | 19.7 ± 4.8** | 77.2 |

Compared with the Control Group, **$P < 0.01$ (Dunnett's test)

The above result suggests that a ClC-2 channel opener is effective for treatment of gastric ulcer.

EXAMPLE 9

(Method)

Mercuric chloride ($HgCl_2$) of 4 mg/kg was intramuscularly administered to male Wistar rats (weight: 245-290 g) to induce ulcer in the large intestine. Thirty minutes before, and 2 and 6 hours after the administration of $HgCl_2$, test substance 2 was subcutaneously administered. The control group received a vehicle. Twenty-four hours after the administration of $HgCl_2$, the animals were bled to death under ether anesthesia. After abdominal incision, the upper portion of the ileocecal opening and the upper portion of the anus were ligated, and the large intestine region from the caecum to the rectum was removed. The removed large intestine was fixed with 1% formalin and then dissected, and the major and minor axes of ulcer were measured with a caliper under a stereoscopic microscope. The product of the major axis multiplied by the minor axis was expressed as the ulcer area. Further, the total ulcer area was calculated in each animal, which was expressed as the gross ulcer area.

(Result)

Table 12 shows the anti-large intestinal ulcer effect.

TABLE 12

Anti-large Intestinal Ulcer Effect

| Group | Dose (µg/kg) | n | Gross Ulcer Area, mm$^2$ (Mean ± S.E.) | Ulcer Inhibitory Rate (%) |
|---|---|---|---|---|
| Control | — | 5 | 29.0 ± 23.5 | — |
| Test Sub. 2 | 10 | 5 | 15.2 ± 15.8 | 54.3 |
| Test Sub. 2 | 1000 | 5 | 3.7 ± 8.3** | 85.3 |

Compared with the Control Group, **P < 0.05 (Dunnett's test)

The above result suggests that a ClC-2 channel opener is effective for treatment of ulcer in the bowel.

EXAMPLE 10

(Method)

Male Wistar rats (weight: 240-270 g) that had been fasted overnight were subjected to abdominal incision under pentobarbital sodium anesthesia. Then a mixed solution of 10% taurocholic acid 3 mL and 0.3% trypsin solution 0.3 mL was antidroicly infused from the bile duct duodenum opening to induce pancreatitis. Thirty minutes before, and 2 and 4 hours after the infusion of the mixed solution of taurocholic acid and trypsin, test substance 2 was subcutaneously administered. The control group received the vehicle. Six hours after the infusion of the mixed solution of taurocholic acid and trypsin, the blood was collected to measure the serum amylase activity.

(Result)

Table 13 shows the anti-pancreatitis effect.

TABLE 13

Anti-pancreatitis Effect

| Group | Dose (µg/kg) | n | serum amylase, IU/L (Mean ± S.E.) | Inhibitory Rate (%) |
|---|---|---|---|---|
| Control | — | 12 | 3141 ± 838 | — |
| Test Sub. 2 | 100 | 9 | 2430 ± 417 | 22.6 |

The above result suggests that a ClC-2 channel opener is effective for treatment of pancreatitis.

EXAMPLE 11

(Method)

Beagle dogs (weight: 8.8-10.3 kg) were used, and under thiopental sodium and α-chloralose anesthesia, their cardiac output was guided from a FJ probe equipped on the aortic arch via a rectangular wave electromagnetic blood flow meter (MFV-3100, Nihon Koden) to a blood flow-indicating unit and recorded in a recorder. The model of cardiac incompetence was prepared in accordance with the following method. A continuous infusion of lactate Ringer solution (5 mL/body/min) having dissolved therein DL-propranolol (0.06 mg/mL) from a catheter inserted into the left femoral vein started diastolic overload. Thirty minutes later, the left anterior descendence (LAD) was ligated. Thirty minutes after ligating the LAD, methoxamine solution was continuously infused from the right femoral vein (5 µg/kg/min), and the infusion of methoxamine solution was increased by 5 µg/kg/min until the cardiac output was reduced by at least 20% from that before the diastolic overload, and the infusion was maximally increased by 20 µg/kg/min. At the time the cardiac output was reduced by at least 20% from that before the diastolic overload, the dose of methoxamine was reduced to 5 µg/kg/min and the infusion of lactate Ringer solution was reduced to 3 mL/kg/min, which was continued until the completion of experiments. Sixty to 90 minutes after the cardiac output was reduced by at least 20% and other hemodynamic parameters were stabled, test substance 2 was administered via a cannula indwelled in the duodenum. The control group received a vehicle. The ratio of the cardiac output at 30 minutes after the administration of test substance 2 as compared to the cardiac output immediately before the administration of test substance 2 or a vehicle was expressed by a relative value (%).

(Result)

Table 14 shows the cardiac output increasing effect.

TABLE 14

Cardiac Output Increasing Effect

| Group | Dose (µg/kg) | n | Relative Cardiac Output, % (Mean ± S.E.) |
|---|---|---|---|
| Control | — | 15 | 97.7 ± 2.13 |
| Test Sub. 2 | 100 | 15 | 108.7 ± 0.47* |
| Test Sub. 2 | 300 | 15 | 117.8 ± 2.42** |

Compared with the Control Group, *P < 0.05, **P < 0.01 (Dunnett's test)

The above result suggests that a ClC-2 channel opener is effective for treatment of cardiovascular system disorder.

What is claimed is:

1. A method for therapeutic treatment of digestive system disorder, which comprises the step of administrating an effective amount of a compound selected from the group consisting of 13,14-dihydro-15-keto-16,16-difluoro prostaglandin $E_1$ and 13,14-dihydro-15-keto-16,16-difluoro-18(S)-methyl-prostaglandin $E_1$ to a subject in need of said treatment, wherein the digestive system disorder is gastric ulcer or ulcer in the bowel.

2. The method of claim 1, wherein the digestive system disorder is gastric ulcer or large intestinal ulcer.

3. A method for therapeutic treatment of pancreatitis, which comprises the step of administrating an effective amount of 13,14-dihydro-15-keto-16,16-difluoro-18(S)-methyl-prostaglandin $E_1$ to a subject in need of said treatment.

4. The method of claim 2, wherein the digestive system disorder is gastric ulcer.

5. The method of claim 2, wherein the digestive system disorder is large intestinal ulcer.

6. The method of claim 1, wherein the compound is 13,14-dihydro-15-keto-16,16-difluoro-18(S)-methyl-prostaglandin $E_1$.

7. The method of claim 1, wherein the compound is 13,14-dihydro-15-keto-16,16-difluoro prostaglandin $E_1$.

* * * * *